United States Patent
Genereux et al.

(10) Patent No.: US 12,268,379 B2
(45) Date of Patent: Apr. 8, 2025

(54) ACCESS CLOSURE WITH BLEED MONITORING

(71) Applicant: Saranas, Inc., Houston, TX (US)

(72) Inventors: Philippe Genereux, New York, NY (US); Robert M. Kipperman, Morristown, NJ (US); Kenneth M. Bueche, Friendswood, TX (US); Zaffer Syed, Houston, TX (US)

(73) Assignee: Saranas, Inc., Houston, TX (US)

( * ) Notice: Subject to any disclaimer, the term of this patent is extended or adjusted under 35 U.S.C. 154(b) by 0 days.

(21) Appl. No.: 18/603,125

(22) Filed: Mar. 12, 2024

(65) Prior Publication Data
US 2024/0215968 A1 Jul. 4, 2024

Related U.S. Application Data

(63) Continuation of application No. 17/548,052, filed on Dec. 10, 2021, now abandoned, which is a
(Continued)

(51) Int. Cl.
*A61B 17/00* (2006.01)
*A61B 5/053* (2021.01)

(52) U.S. Cl.
CPC .......... *A61B 17/0057* (2013.01); *A61B 5/053* (2013.01); *A61B 2017/0065* (2013.01); *A61B 2017/00663* (2013.01)

(58) Field of Classification Search
CPC .......... A61B 17/0057; A61B 17/06061; A61B 2017/00004; A61B 2017/00026;
(Continued)

(56) References Cited

U.S. PATENT DOCUMENTS

| 6,696,757 B2 | 2/2004 | Yunus et al. |
| 8,155,756 B2 | 4/2012 | Yang et al. |

(Continued)

FOREIGN PATENT DOCUMENTS

| JP | H06339483 A | 12/1994 |
| JP | 2006503645 A | 2/2006 |

(Continued)

OTHER PUBLICATIONS

International Search Report received May 19, 2020, in counterpart International Application Serial No. PCT/US20/13002.
(Continued)

*Primary Examiner* — Mohamed G Gabr
(74) *Attorney, Agent, or Firm* — Botos Churchill IP Law LLP

(57) ABSTRACT

A blood vessel access closure device includes an inner blood vessel wall support member and an outer blood vessel wall support member. The closure device also includes a deployment member and an electrode. The deployment member is configured to draw the inner and outer blood vessel wall support members towards each other when the inner and outer blood vessel wall members are deployed on opposite sides of a blood vessel wall during closure of a hole in the blood vessel wall. The electrode is configured to be attached to the deployment member and configured to be used to measure impedance.

11 Claims, 6 Drawing Sheets

Related U.S. Application Data continuation of application No. 16/738,176, filed on Jan. 9, 2020, now Pat. No. 11,224,414.

(60) Provisional application No. 62/790,906, filed on Jan. 10, 2019.

(58) Field of Classification Search
CPC ........... A61B 2017/00115; A61B 2017/00221; A61B 2017/0065; A61B 2017/00654; A61B 2017/00659; A61B 2017/00663; A61B 2017/00951; A61B 2017/0495; A61B 2017/22038; A61B 2505/05; A61B 2560/0412; A61B 2560/0431; A61B 2560/0468; A61B 2562/0209; A61B 2562/043; A61B 2562/166; A61B 5/0002; A61B 5/02042; A61B 5/053; A61B 5/0538; A61B 5/6833; A61B 5/6847; A61B 5/688; A61B 5/742; A61B 5/746
See application file for complete search history.

(56) References Cited

U.S. PATENT DOCUMENTS

| | | | |
|---|---|---|---|
| 8,346,372 B2 | 1/2013 | Yang et al. | |
| 2005/0101965 A1* | 5/2005 | Ryan | A61B 18/1442 606/96 |
| 2006/0173492 A1* | 8/2006 | Akerfeldt | A61B 17/0057 606/232 |
| 2007/0083232 A1 | 4/2007 | Lee | |
| 2010/0160999 A1 | 6/2010 | Epstein et al. | |
| 2011/0282162 A1* | 11/2011 | Razavi | A61B 5/6883 606/34 |
| 2012/0022562 A1 | 1/2012 | Willard | |
| 2016/0029906 A1 | 2/2016 | Tompkins et al. | |
| 2017/0049359 A1 | 2/2017 | Arevalos et al. | |

FOREIGN PATENT DOCUMENTS

| | | |
|---|---|---|
| JP | 2007521084 A | 8/2007 |
| JP | 2009056318 A | 3/2009 |
| JP | 2019524393 A | 9/2019 |
| JP | 2022518393 A1 | 3/2022 |
| WO | 2004037315 A2 | 5/2004 |
| WO | 2018031539 A1 | 2/2018 |
| WO | 2020146688 A1 | 7/2020 |

OTHER PUBLICATIONS

Office Action from corresponding Japanese Patent Application No. 2023-192192 dated Nov. 12, 2024 (10 pp.).

* cited by examiner

ACCESS CLOSURE WITH BLEED MONITORING

CROSS-REFERENCE TO RELATED APPLICATIONS

This application is a continuation of U.S. patent application Ser. No. 17/548,052 filed Dec. 10, 2021, which is a continuation of and claims priority to U.S. application Ser. No. 16/738,176 filed Jan. 9, 2020, now U.S. Pat. No. 11,224,414. U.S. Pat. No. 11,224,414 claims priority to U.S. Provisional Application No. 62/790,906, filed Jan. 10, 2019. All of the aforementioned patent applications are hereby incorporated by reference.

BACKGROUND

Some medical procedures involve accessing a patient's blood vessel. For example, catheterizations involve inserting a catheter into a blood vessel to access other parts of the person such as the heart. To access a blood vessel, a needle is first inserted through the person's skin and into the blood vessel. A wire is then inserted through the needle and the needle is then removed. Other components, such as an introducer sheath are then inserted through the hole in the blood vessel wall While some vessel wall holes may close themselves, not all do. At the end of the medical procedure, the hole in the blood vessel may need to be manually closed such as through use of any of a variety of blood vessel access closure devices and techniques.

SUMMARY

Various examples of blood vessel access closure devices are disclosed that include the ability for bioimpedance to be measured. The impedance of the body around the site of a blood vessel hole being closed can be used to determine if the hole has been adequately closed, or whether the hole is still leaking blood.

In one example, a blood vessel access closure device includes an inner blood vessel wall support member and an outer blood vessel wall support member. The closure device also includes a deployment member and an electrode. The deployment member is configured to draw the inner and outer blood vessel wall support members towards each other when the inner and outer blood vessel wall members are deployed on opposite sides of a blood vessel wall during closure of a hole in the blood vessel wall. The electrode is configured to be attached to the deployment member and configured to be used to measure impedance.

In another example, a blood vessel access closure device includes a suture wire and an electrode. The suture wire is configured to close a hole in a blood vessel. The electrode is coupled to the suture wire and is configured to be attached to the deployment member and configured to be used to measure impedance.

BRIEF DESCRIPTION OF THE DRAWINGS

For a detailed description of various examples, reference will now be made to the accompanying drawings in which.

DETAILED DESCRIPTION

Blood vessel access closure systems are used to close a hole in a blood vessel. However, it is possible that blood still leaks through the hole in the blood vessel wall even after use of the access closure device. In accordance with the disclosed examples, the access closure systems described herein include the ability to measure electrical impedance in the area around the blood vessel hole. The impedance of blood is different than the impedance of other body tissues and thus an accumulation of blood on the outside of the blood vessel in the area around the hole being closed indicates that blood is still leaking through the hole despite the application of the access closure device.

Figure 1:
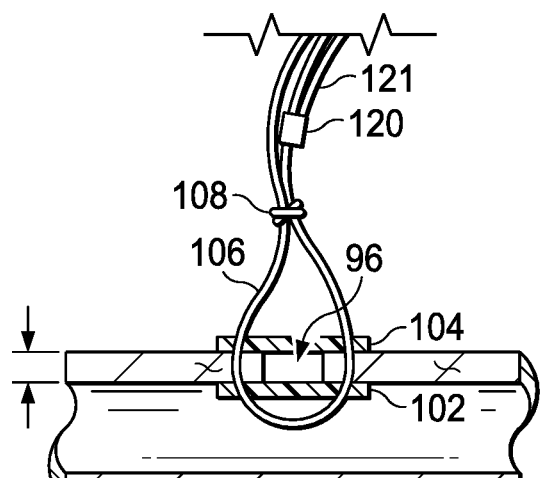
FIG. 1 illustrates an access closure system with an electrode usable to detect bleeding.

FIG. 1 shows an example of a portion of an access closure system. The access closure system in this example includes an inner blood vessel wall support member 102, an outer blood vessel wall support member 104, and a suture wire 106 with an electrode 120 slid over the suture wire 106. The access closure system is shown to close a hole 96 in blood vessel 95. The electrode 120 is slid over the suture wire and is attached to electronics (described below) with a conductive wire. The inner blood vessel wall support member 102 is positioned inside the blood vessel at the hole 96. The outer blood vessel wall support member 104 is positioned opposite the inner blood vessel wall support member at the hole 96. The suture wire 106 is a type of deployment member usable to draw the inner and outer blood vessel wall support members 102, 104 towards each other to thereby seal the hole 96.

Figure 2:
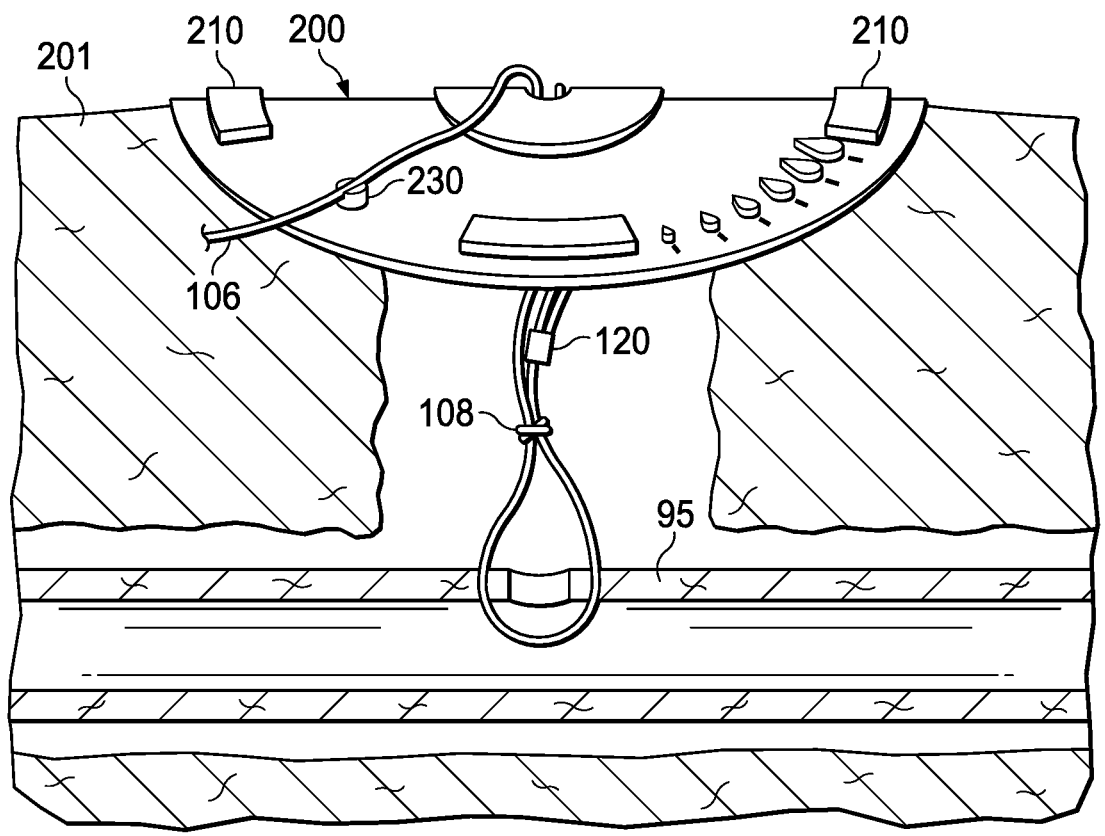
FIG. 2 illustrates another example of an access closure system that can detect bleeding.

FIG. 2 shows a person's leg 201 in which blood vessel 95 has a hole to be closed. An adhesive patch 200 is shown on the skin of the person's leg 201. The adhesive patch 200 includes one or more electrodes 210 connected to a circuit (e.g., integrated circuit, not shown) integrated into the patch. The electrode 120 on the suture wire also is connected to the circuit. The circuit measures the electrical impedance between electrode 120 and one or more of the patch's electrodes 210. Based on the impedance measurements, a determination can be made as to whether the hole in the blood vessel 95 has been adequately sealed. The patch 200 includes a suture wire clip 230. The suture wire clip 230 grabs the suture wire to provide strain relief and access for later removal.

In FIG. 1, a knot 108 is formed in the suture wire 106 and the electrode 120 is positioned on the suture wire above the knot 108. The knot is moved down the suture wire to draw the inner and outer blood vessel support members 102, 104 together. In this example, the suture wire 106 itself may not be electrically conductive, but the electrode 120 is electrically conductive and connected to the patch's circuit via a separate wire 121.

Figure 3:
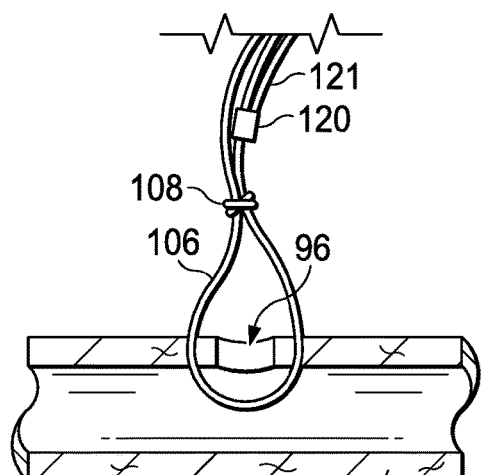
FIG. 3 illustrates yet another access closure system that can detect bleeding.

FIG. 3 shows an example of an access closure system that does not include inner and outer blood vessel wall support members. Instead, suture wire 106 is used to close the hole 96. Electrode 120 is coupled to the suture wire 106 and used to measure impedance to detect a possible bleed.

Figure 4:
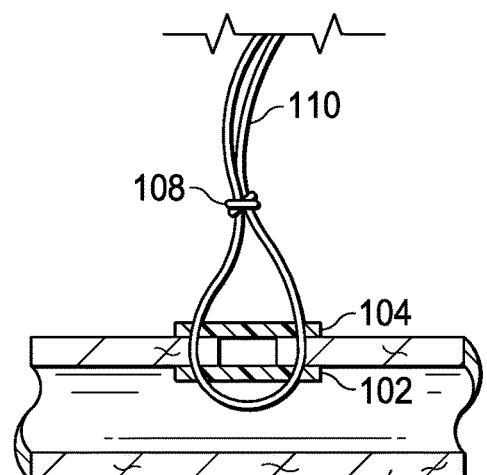
FIG. 4 shows another example of an access closure system to detect bleeding.

FIG. 4 shows another example of an access closure system that includes inner and outer blood vessel wall support members. In this example, the suture wire 110 is electrically conductive, and thus no separate electrode 120 is included. Impedance can be measured by the patch's circuit between the patch's electrode(s) and the conductive suture wire 110. The conductive suture wire is insulated with a portion of the conductive wire exposed at a predefined location(s) along the wire.

To measure impedance, the patch's circuit may inject a predetermined current magnitude through one pair of electrodes (including the electrode 120 near the site of the blood vessel 95) and measure the resulting voltage using a different set of electrodes. One of the electrodes may be used for both the current injection and voltage measurement. The ratio of voltage to current equals impedance. Alternatively, the circuit may use one pair of electrodes (including electrode 120) to apply a voltage of a predetermined amplitude and measure the resulting current. The current or voltage applied to the electrodes may be AC or DC. Impedance measurements made at certain frequencies may provide more useful information than at other frequencies. At certain frequencies, it may be difficult to detect a bleed, whereas at other frequencies, bleed detection is easier. In one example, the frequency used for the impedance measurements are in the range of 1000 Hz to 200 KHz, although a different frequency range may be acceptable as well. Additional information regarding impedance measurements may be found in US. Pat. Pub. No. 2017/0049359 which incorporated herein by reference.

Figure 5:
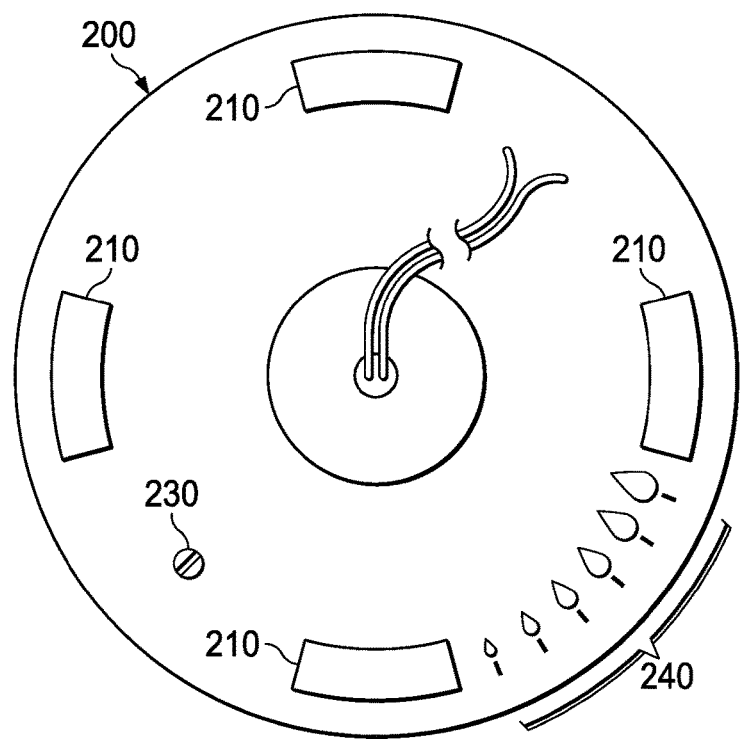
FIG. 5 shows additional detail of the example adhesive patch.

FIG. 5 shows a top-down view of adhesive patch 200. The patch 200 in the example of FIG. 5 includes one or more visual indicators 240 which provide visual feedback as to whether a bleed condition has been detected, and the severity of the bleed condition. For example, the more indicators 240 that are illuminated means that a more severe (e.g. longer lasting) bleed condition has been detected. The circuit contained in the adhesive patch may be battery operated. The patch 200 in FIG. 5 is generally circular. In one example, the diameter of the patch is 2 to 3 inches. The electrodes 210 are positioned around the outer periphery of the patch.

Figure 6:
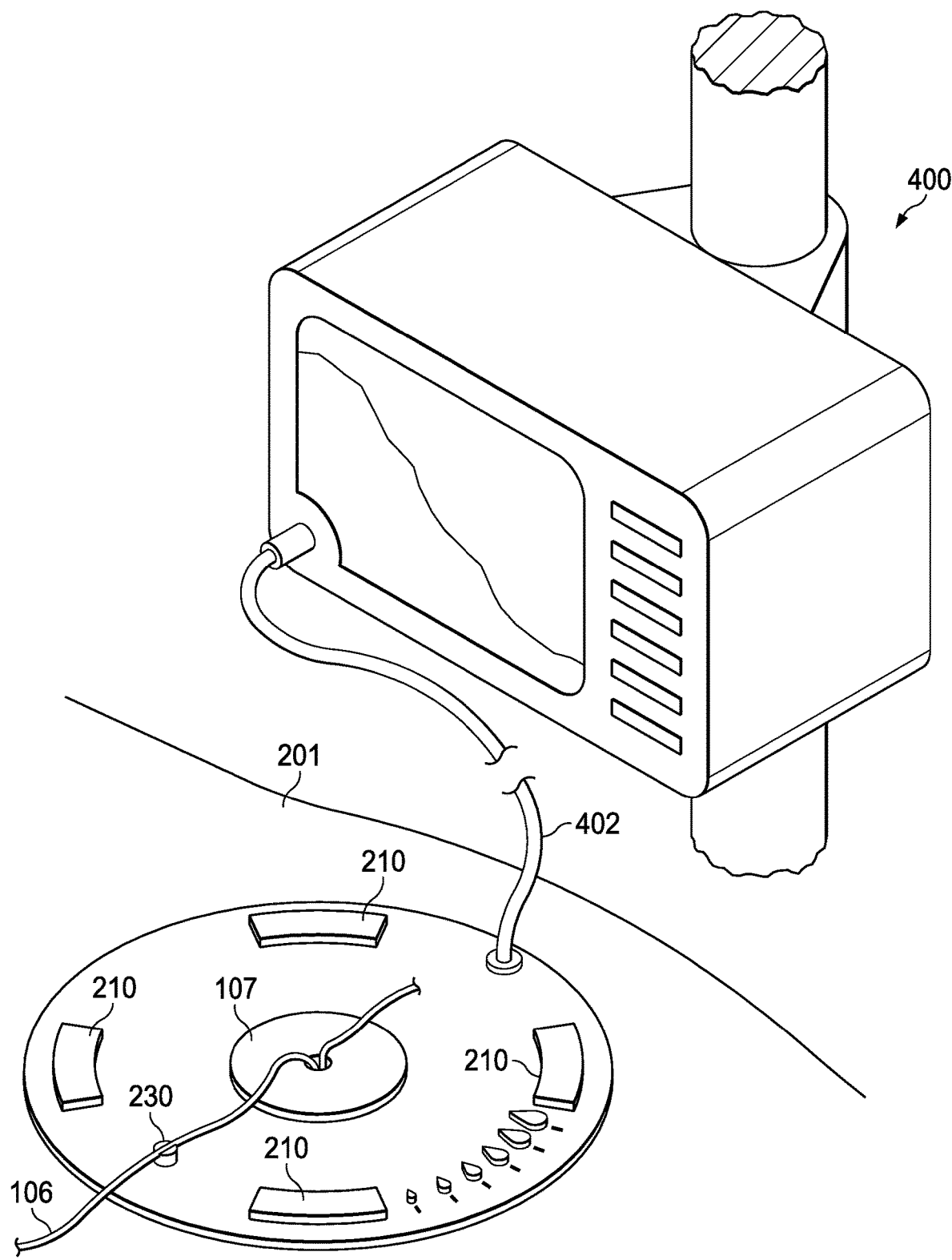
FIG. 6 illustrates an example in which the adhesive patch is connected to a bedside monitor.

FIG. 6 shows another example of an adhesive patch. The adhesive patch in this example includes a wired interface that can be connected via a cable 402 to a bedside monitor 400. Signals indicative of the measured impedance may be displayed on the monitor's display. The patch's circuit may measure impedance and provide impedance values to the bedside monitor, or the patch's circuit may provide current and voltage values to the bedside monitor and the bedside monitor may compute impedance. In another example, the interface between the patch and the bedside monitor may be wireless, instead of wired as shown in FIG. 6. The bedside monitor also may provide the electrical power for the patch's electronics.

Figure 7:
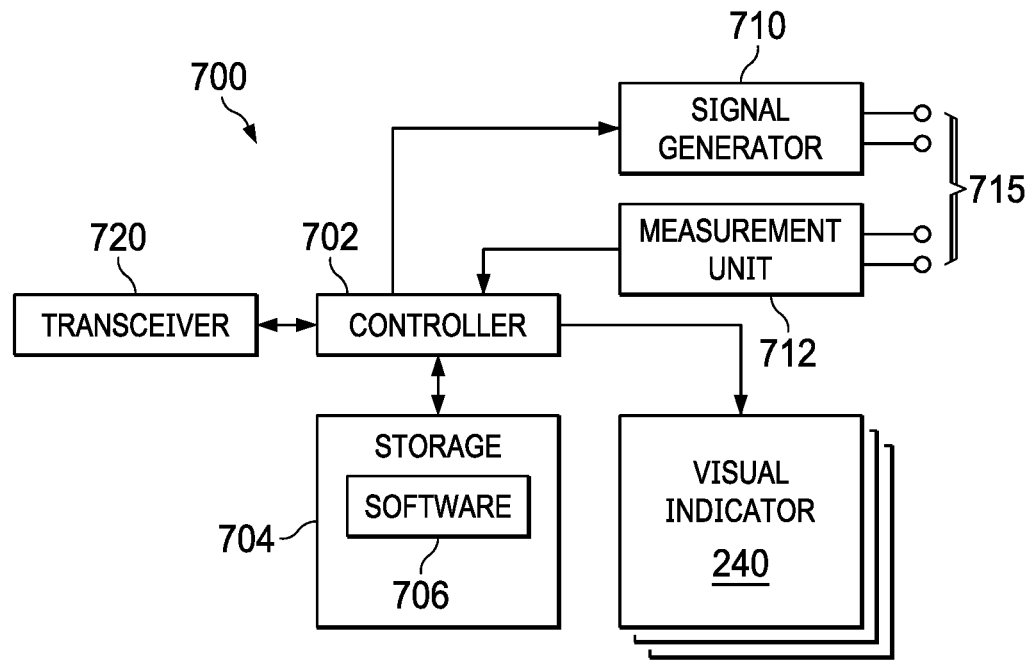
FIG. 7 shows an example of the electronics included in the adhesive patch operative to measure impedance to detect bleeding.

FIG. 7 shows an example of the circuit 700 included in the adhesive patch 200. In this example, the circuit includes a controller 702, storage 704, visual indicators 240, a signal generator 710, a measurement unit 712, and a transceiver 720. The controller 702 may be a hardware processor that executes software 706 stored in storage 704. Storage 704 may comprise volatile storage (e.g., random access memory) and/or non-volatile storage (e.g., read-only memory). The functionality attributed herein to that patch's circuit is implemented by the controller 702 upon execution of its software 706. Each visual indicator 240 may comprise a light emitting diode (LED). The electrodes (e.g. electrode 120, patch electrode 210) are coupled to one or more of the signal generator 710 and measurement unit 720. Upon command by the controller 702, the signal generator 710 generates a predetermined signal (e.g. current or voltage) to be provided to two of the electrodes, and the measurement unit 712 measures the resulting voltage or current as explained above. At least one of the electrodes used by the measurement unit 712 is the electrode near the site of the blood vessel hole being sealed (e.g., electrode 120 or conductive suture wire 110). The controller 702 may provide the impedance values to the transceiver 720 for transmission to an external device (e.g., bedside monitor 400). In one example, the transceiver 720 provides a wired interface. In another example, the transceiver 720 provides a wireless interface. An example of a wireless interface includes Bluetooth.

Figure 8:
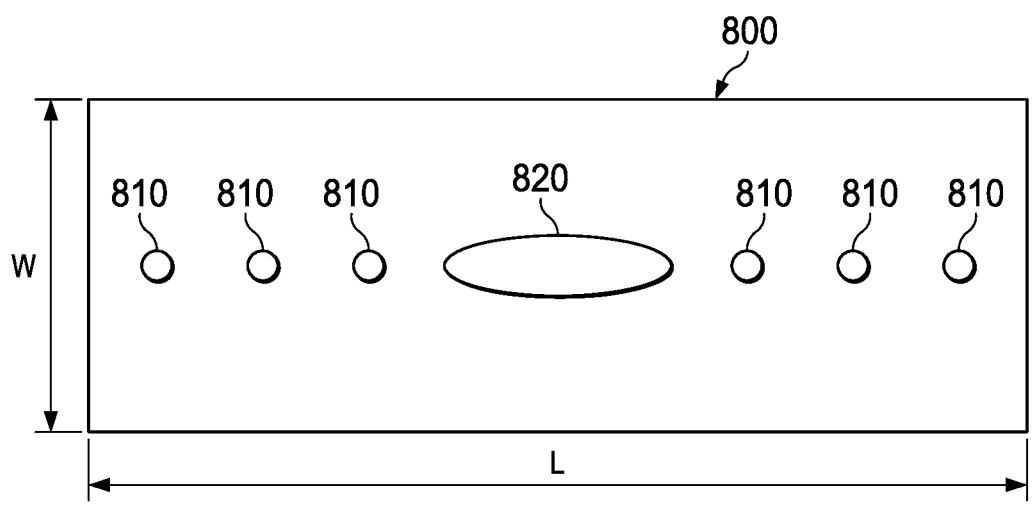
FIG. 8 shows an example of an adhesive patch with multiple electrodes arranged in a line.

In the example of FIG. 5, the adhesive patch was approximately circular. In the example of FIG. 8, the adhesive patch 800 is approximately rectangular. The rectangular shape of the patch 800 has a width (W) and a length (L), where L is larger than W. In one example, W is approximately 1 inch and L is approximately 6 inches. Multiple electrodes 810 are positioned along an axis of the patch parallel to length L (i.e., along the long axis of the rectangle). The patch 800 is positioned near the site of the blood vessel hole being closed and any or all of the electrodes 810 can be used to measure impedance between each such electrode and electrode 120 (adjacent the blood vessel). Providing multiple electrodes along the long axis of the patch helps to ensure a bleed is detected regardless of the location of the accumulation of blood near the blood vessel wall's hole.

In another example, the patch has no battery. Instead, the patch has a coil of wire or other type of antenna that can receive wireless power from an external device (e.g., a handheld wand). When the external device is brought near the patch, the patch's circuit is powered up, initiates an impedance measurement, and transfers one or more values indicative of impedance to the external device.

Another example includes an electrode 120 that is constructed of a conductive bioabsorbable polymer that is not removed. Instead, following use of the electrode during a medical procedure to detect bleeding, the electrode remains in the body and is reabsorbed. Suitable polymers for such an electrode are described in U.S. Pat. No. 6,696,575, incorporated herein by reference.

Figure 9:
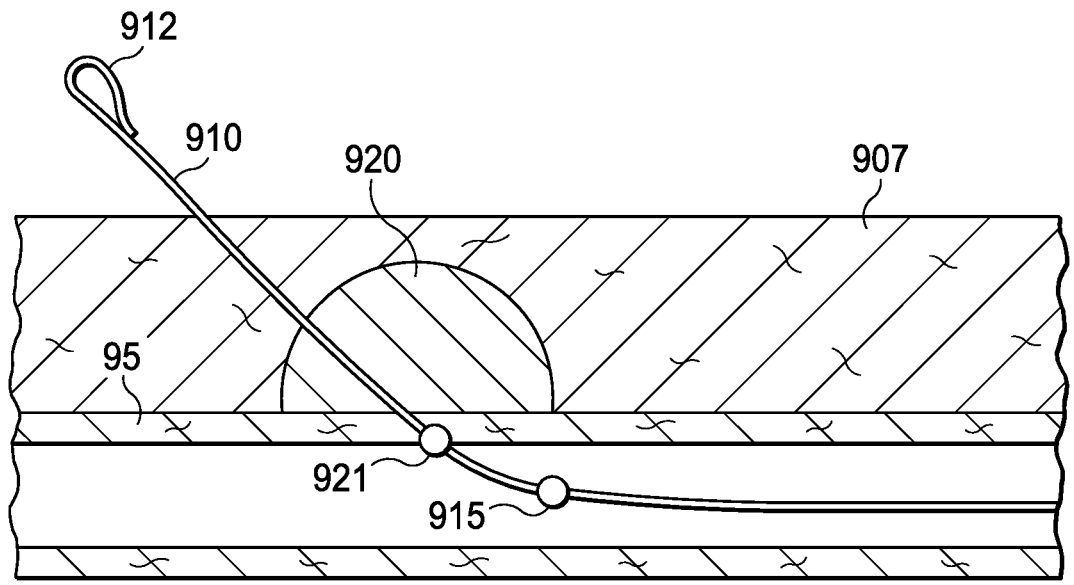
FIG. 9 shows an example of the use of a collagen plug to seal a hole in a blood vessel in conjunction with a guidewire having an electrode usable to measure impedance for bleed detection.

FIG. 9 shows an example of the use of a collagen plug 920 to seal a hole 921 in a blood vessel 95. A guidewire 910 is shown inserted through the patient's skin 907, through the collagen plug 920, and into the blood vessel 95. The guidewire 910 may been used during the patient's catherization. The guidewire 910 includes an electrode 915 and may include additional electrodes as well. An electrical connector 912 is connected to the electrode 915 via a conductor (e.g., a wire not shown, or the guidewire itself). The example electrode 915 is shown on the guidewire inside the blood vessel and can be used to measure impedance between electrode 915 and another electrode, for example, one or more of the patch electrodes 210, 810. The connector 912 can be connected to a circuit (e.g., circuit 700) to use the guidewire's electrode and another electrode (e.g., an electrode on the patch or another electrode on the guidewire) to measure impedance to detect a bleed.

In one example, at the end of a vascular access procedure, the guidewire is left in the vessel to monitor for bleed complications until it is determined that the risk of bleeding is sufficiently low. The physician deploys an access closure device in the form of a collagen plug 920 that seals around the guidewire 910 and hole 921. After it is determined that the risk of bleeding is low, the physician may then remove the guidewire 910 by pulling the guidewire through the collagen plug 920 and leg tissue. The collagen plug 920 may remain in place maintaining a seal around the blood vessel wall.

Figure 10:
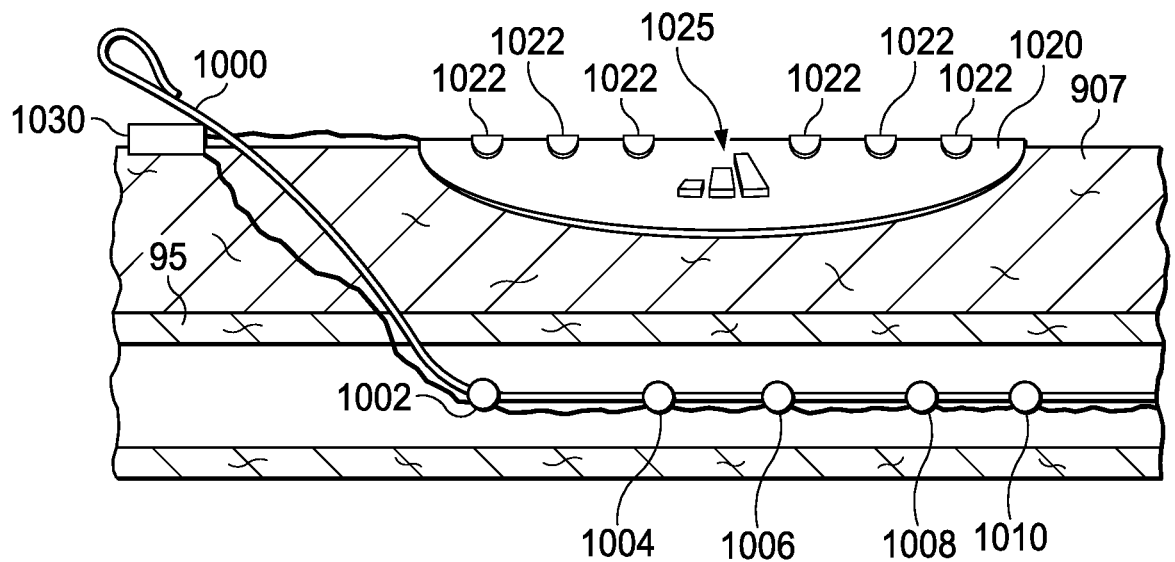
FIG. 10 illustrates that multiple impedance zones can be monitored across the electrodes of the guidewire and between guidewire electrodes and surface patch electrodes.

FIG. 10 shows an example of a guidewire 1000 having multiple electrodes 1002, 1004, 1006, 1008, and 1010. Five electrodes are shown on the guidewire 1000 in this example, but fewer than five or more than five electrodes may be provided on the guidewire in other examples. An adhesive patch 1020 (such as that described herein) is shown on the patient's skin 907 generally above the site of the access point into blood vessel 95. An electronics module 1030 is electrically connected to the electrode 1022 on patch 1020 as well as to electrodes 1002-1010 on the guidewire 1000. The electronics module 1030 may include some or all of the components shown in FIG. 7, and may be provided separate from the patch or on the patch itself. The electronics module 1030 may measure the impedance between electrodes on the guidewire 1000 or between one or more electrodes on the guidewire 1000 and one or more electrodes 1022 on the patch 1020. As such, multiple different impedance "zones" may be measured using any combination of electrodes 1022 and 1002-1010.

Figure 11:
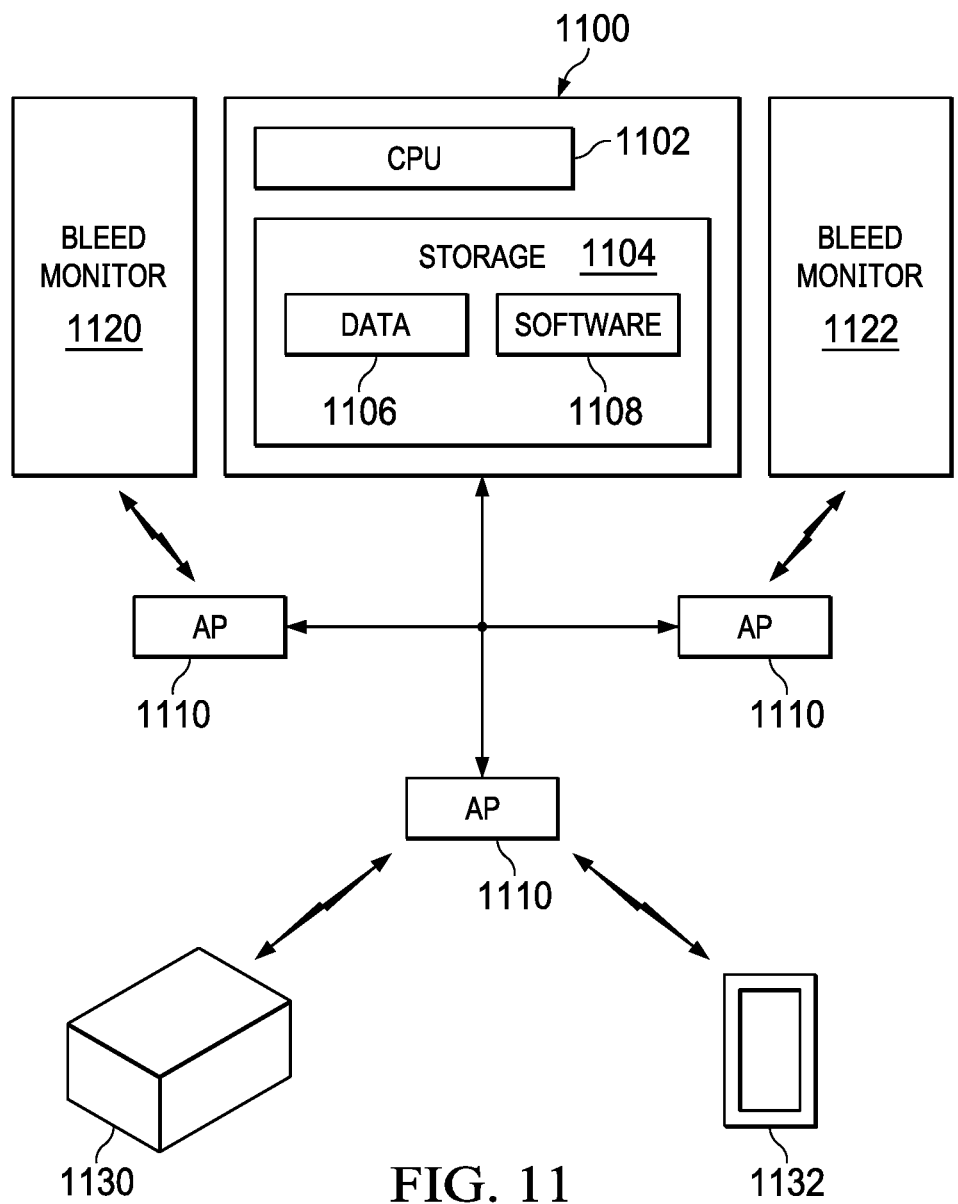
FIG. 11 illustrates a system for the centralized collection of bleed monitoring related data and the transmissions of bleed alerts to healthcare professionals.

FIG. 11 shows a system, such as may be implemented in a hospital. The system includes one or more bleed monitors 1120, 1122, a central control system 1100, wireless access points 1110, and portable devices 1130, 1132. Each bleed monitor 1120, 1122 includes any of the bleed detection implementations described above. Each bleed monitor 1120, 1122 may transmit (e.g., wirelessly) patient-related bleed information through a corresponding access point 1110 to the central control system 1100. The patient-related bleed information may include impedance values, bleed level indicators, etc. generated locally for each patient.

The central control system 1110 includes a processor 1102 and storage 1104 (e.g., memory, hard drive, etc.). The storage 1104 may store the received patent-related bleed information and software to be executed by the processor 1102. In one example, the central control system 1110 is a computer. The central control system 1110 may transmit alerts for a given patient to that patient's physician who carries one of the portable devices 1130, 1132. As such, a patient's physician may be kept abreast of the status of that physician's patients (e.g., whether the patient is experiencing a bleed, the severity of the bleed, etc.).

Modifications are possible in the described embodiments, and other embodiments are possible, within the scope of the claims.

What is claimed is:

1. A blood vessel access closure device, comprising:
   an inner blood vessel wall support member configured to be positioned inside a blood vessel;
   an outer blood vessel wall support member configured to be positioned outside the blood vessel;
   a deployment member configured to draw the inner and outer blood vessel wall support members towards each other when the inner and outer blood vessel wall members are deployed on opposite sides of a blood vessel wall during closure of a hole in the blood vessel wall;
   a first electrode configured to be attached to the deployment member, the first electrode being bioabsorbable;
   multiple visual indicators; and
   a circuit coupled to the first electrode and the multiple indicators, the circuit configured to determine a value indicative of impedance using the first electrode, determine that a bleed is occurring based on the value indicative of impedance, and cause the multiple visual indicators to indicate a severity of the bleed.

2. The blood vessel access closure device of claim 1, wherein the deployment member comprises a conductive suture wire attached to the first electrode.

3. The blood vessel access closure device of claim 1, further comprising an adhesive patch configured to be placed on a person's skin over a blood vessel access location, the adhesive patch comprising a second electrode coupled to the circuit.

4. The blood vessel access closure device of claim 1, wherein the circuit is configured to transmit a wireless signal indicative of the value indicative of impedance.

5. The blood vessel access closure device of claim 1, further comprising an adhesive patch configured to be placed on a person's skin over the blood vessel, the adhesive patch comprising a plurality of electrodes.

6. The blood vessel access closure device of claim 5, wherein the circuit is configured to use the first electrode and one or more of the plurality of electrodes on the adhesive patch to determine multiple values indicative of impedance values at different locations.

7. The blood vessel access closure device of claim 5, wherein the adhesive patch comprises the multiple visual indicators.

8. The blood vessel access closure device of claim 5, wherein the adhesive patch has a rectangular shape, the rectangular shape having a width and a length, and the plurality of electrodes are positioned along the length.

9. The blood vessel access closure device of claim 5, wherein the adhesive patch is circular.

10. The blood vessel access closure device of claim 1, further including:
    a guide wire including multiple electrodes; and
    an adhesive patch configured to be placed on a person's skin over a blood vessel access location, the adhesive patch comprising multiple electrode;
    wherein the circuit is configured to determine the value indicative of impedance between (a) any of the multiple electrodes on the adhesive patch and (b) the first electrode and any of the multiple electrodes on the guide wire to determine that the bleed is occurring.

11. The blood vessel access closure device of claim 1, wherein the circuit is configured to determine the severity of the bleed based on a length of time that the bleed has been occurring.

* * * * *